United States Patent
Head

(10) Patent No.: US 8,469,962 B1
(45) Date of Patent: Jun. 25, 2013

(54) PROSTHETIC SOCKET ALIGNMENT

(76) Inventor: William C. Head, McKinney, TX (US)

( * ) Notice: Subject to any disclaimer, the term of this patent is extended or adjusted under 35 U.S.C. 154(b) by 345 days.

(21) Appl. No.: 12/371,308

(22) Filed: Feb. 13, 2009

Related U.S. Application Data

(63) Continuation-in-part of application No. 12/332,109, filed on Dec. 10, 2008.

(51) Int. Cl.
*A61B 17/58* (2006.01)
*A61B 17/60* (2006.01)
*A61F 2/00* (2006.01)

(52) U.S. Cl.
USPC ............................................................ 606/91

(58) Field of Classification Search
USPC ........................................ 606/91, 96–99, 104
See application file for complete search history.

(56) References Cited

U.S. PATENT DOCUMENTS

| | | | |
|---|---|---|---|
| 5,030,219 A | 7/1991 | Matsen et al. | |
| 5,953,683 A | 9/1999 | Hansen et al. | |
| 6,156,069 A | 12/2000 | Amstutz | |
| 6,245,111 B1 | 6/2001 | Shaffner | |
| 7,433,798 B2 | 10/2008 | Townsend et al. | |
| 2003/0130741 A1 | 7/2003 | McMinn | |
| 2005/0107799 A1 | 5/2005 | Graf et al. | |
| 2006/0058886 A1 | 3/2006 | Wozencroft | |
| 2006/0161167 A1* | 7/2006 | Myers et al. | 606/91 |
| 2008/0021479 A1 | 1/2008 | Penenberg | |
| 2008/0196911 A1 | 8/2008 | Krapf et al. | |
| 2010/0114237 A1* | 5/2010 | Giftakis et al. | 607/45 |
| 2010/0137869 A1* | 6/2010 | Borja et al. | 606/88 |
| 2010/0137871 A1* | 6/2010 | Borja | 606/91 |

OTHER PUBLICATIONS

Definition of "Inclinometer," Wikipedia, http://en.wikipedia.org/wiki/Inclinometer, Jan. 27, 2009, pp. 1-3.
Gehring, J., "Gravity Inclinometer," The Tool Shed, http://www.craftsofnj.org/toolshed/articles/Gravity%20inclinometer/GRAVITY%20INCLINOMETERS.htm, Crafts of New Jersey, Feb. 2002, pp. 1-6.
GlobalSpec Engineering Search Engine, search results for "Tilt Sensors and Inclinometers," http://sensors-transducers.globalspec.com/Industrial-Directory/Tilt_Sensors_and Inclinometers, search run Feb. 6, 2009, pp. 1-5.
Hussain, B., "How Does an Inclinometer Work?," https://www.amazines.com/article_detail.cfm/145829?articleid=145829, Aug. 31, 2006, pp. 1-4.
Jonathan, B., "How Does an Inclinometer Work?," Ezine @rticles, http://ezinearticles.com/?How-Does-An-Inclinometer-Work?&id=276738, Aug. 22, 2006, pp. 1-5.
Microstrain ADIS16209 High Accuracy, Dual-Axis Digital Inclinometer and Accelerometer product information, Rev. A, Jan. 30, 2008, 17 pp., Microstrain, Inc., Norwood, MA.

* cited by examiner

*Primary Examiner* — Sameh Boles
(74) *Attorney, Agent, or Firm* — Katarzyna Brozynski

(57) ABSTRACT

Methods, systems and devices for properly positioning and aligning a prosthetic socket into a bone cavity of a patient. The methods involve placing a guide piece, in bone that is close to the bone cavity, according to the position and alignment of a trial prosthetic socket previously fitted in a desired position and alignment in the bone cavity and then, after removing the trial, positioning and aligning the prosthetic socket in the bone cavity using the guide piece's position and alignment for guidance. A tilt sensing device is used to show the tilt or angle of devices used in the positioning and alignment procedure.

15 Claims, 20 Drawing Sheets

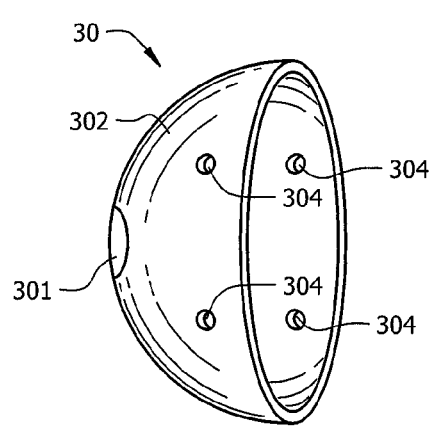 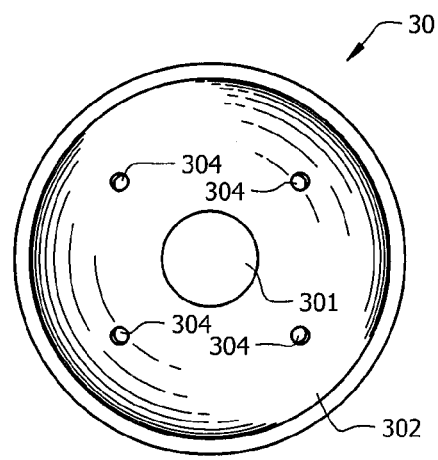
FIG. 3A  FIG. 3B
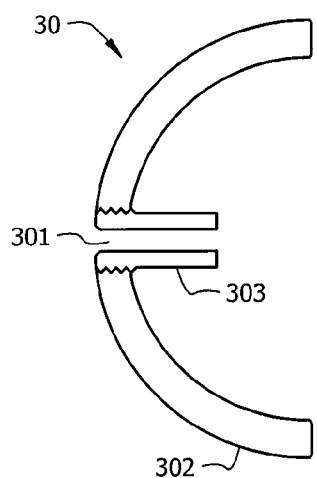 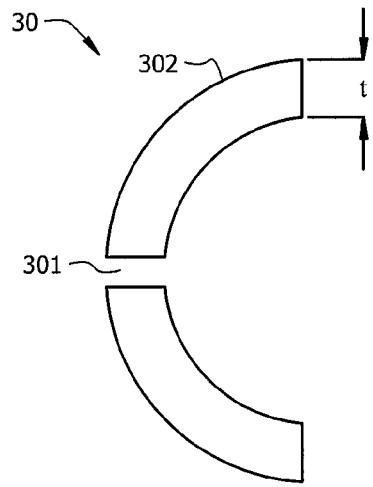
FIG. 3C  FIG. 3D
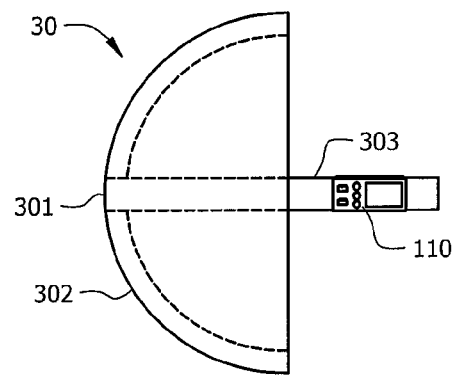
FIG. 3E

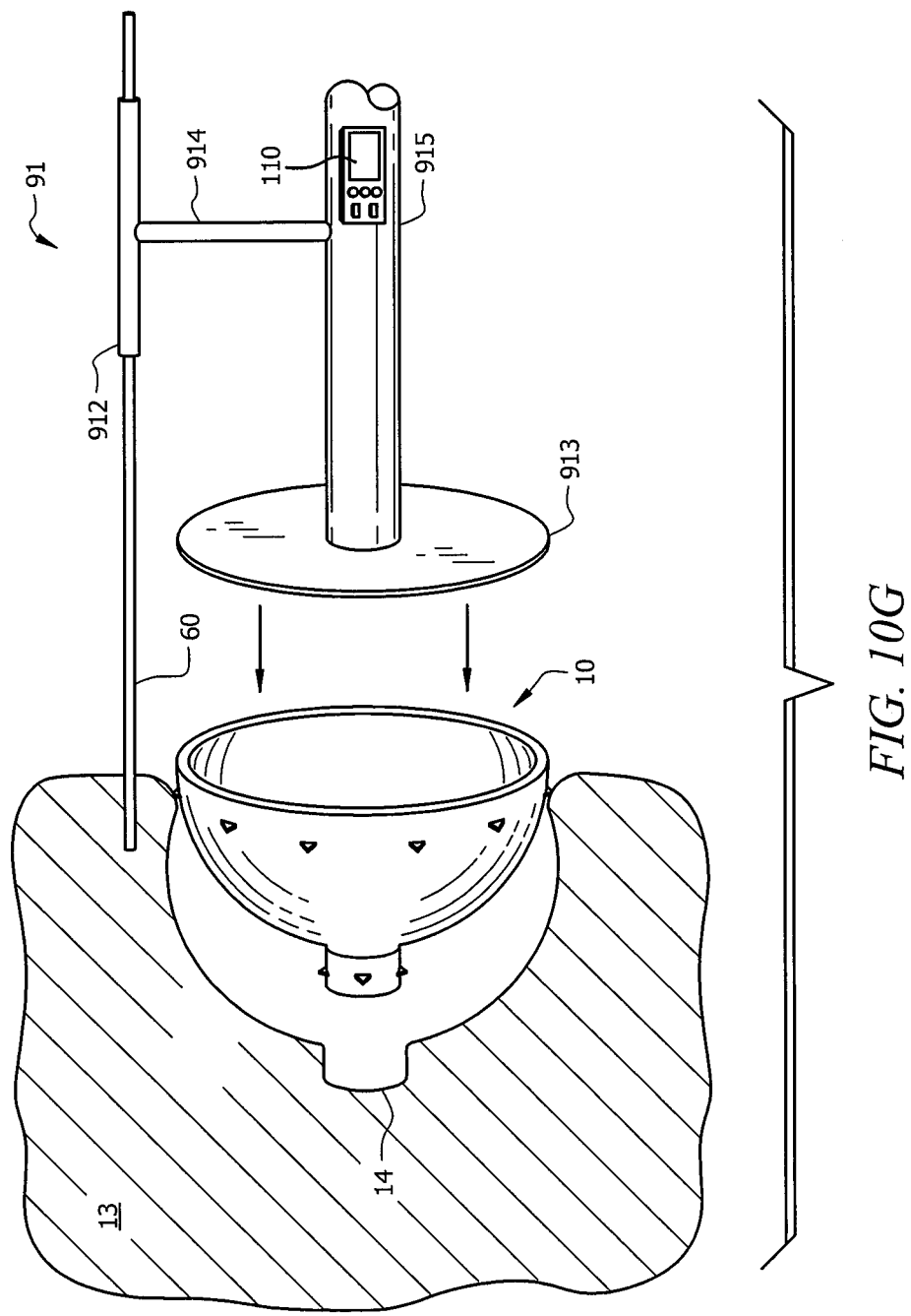

PROSTHETIC SOCKET ALIGNMENT

CROSS-REFERENCE TO RELATED APPLICATIONS

This application is a continuation-in-part of U.S. patent application Ser. No. 12/332,109, entitled "PROSTHETIC SOCKET ALIGNMENT," filed Dec. 10, 2008, and is related to co-pending, commonly owned U.S. patent application Ser. No. 12/360,512, entitled "SYSTEM AND METHOD FOR RESURFACING HIP REPLACEMENT," filed Jan. 27, 2009, the disclosures of which are hereby incorporated herein by reference.

TECHNICAL FIELD

The current invention is in the field of prosthetic devices. In particular, the current invention involves the proper alignment of prosthetic devices.

BACKGROUND OF THE INVENTION

A prosthetic device is an artificial device used to replace a body part. For example, since the 1960's, prosthetic devices have been used in hip replacement surgery. Hip replacement surgery is an increasingly common surgery used to treat joint failure in patients. Joint failures are often caused by diseases such as osteoarthritis, rheumatoid arthritis etc. Treating joint failures by hip replacement typically involves replacing the ball on the femur (the bone that extends from the pelvis to the knee) with a prosthetic ball and replacing the socket in the hip with a prosthetic socket. The socket is part of the pelvis and the ball fits into the socket.

Though medical practitioners have been performing hip replacement surgeries for more than half a century, at least two significant problems persist with this medical procedure. First, the prosthetic ball sometimes dislocates from the prosthetic socket (i.e., the prosthetic ball comes out of the prosthetic socket). Improper alignment of the prosthetic ball and socket during hip replacement surgery is one factor that causes dislocation of the prosthetic ball from the prosthetic socket after surgery. Second, depending to some extent on the materials used to make the prosthetic ball and socket, excessive wear of those materials may occur as the prosthetic ball moves in the prosthetic socket during use. As with the dislocation problems, improper alignment of the ball and socket during surgery is one major factor that causes excessive wear during use. For example, excessive wear occurs when the prosthetic ball rubs excessively on one edge of the socket. This is known as edge loading. Wear debris, such as formed by edge loading in the joint, can cause major complications such as inflammation and loosening of the prosthetic components. Moreover, when the prosthetic components wear out or loosen, they have to be replaced in another hip replacement surgery.

Because of the problems associated with improperly aligned prosthetic sockets and balls, medical practitioners generally make every effort to try and properly align these devices during surgery. Most medical practitioners rely on their experience to view the bone cavity and manually place the prosthetic socket in the proper position. For example, the proper alignment of the hemispherical socket in the acetabula (the cup-shaped cavity in the pelvis into which the ball-shaped head of the femur fits) is typically attained when it is about 40° to 45° of abduction. Additionally, when the prosthetic socket is properly aligned in the acetabula, the open area of the socket typically should be about 10° to 20° of anteversion, i.e., facing forward. It should be noted that though the abduction angle is typically about 40° to 45° and the anteversion angle is typically about 10° to 20°, variations outside these ranges are possible and the embodiments of the invention disclosed herein may be used in instances outside of the typical ranges.

Particularly because medical practitioners are now doing surgeries with smaller incisions than have traditionally been used, it is not uncommon that manual fitting of a prosthetic socket during hip surgery results in the prosthetic socket being placed at an angle of 50° to 60° and even facing slightly backward (retroversion). Such improper alignment generally results in dislocations of the hip and excessive wear of the prosthetic ball and socket after surgery. To improve upon manual alignment of prosthetic sockets, medical practitioners have tried to use positioning devices based on x-ray, fluoroscopy, MRI and other electronic technology. Despite these technologies, improper alignments of prosthetic balls and sockets persist and these improper alignments in turn cause complications such as dislocations and excessive wear. Moreover, apart from the limited success with the current positioning devices, these devices are expensive to make and operate.

BRIEF SUMMARY OF THE INVENTION

The present invention is directed to systems, devices and methods which properly position and align a prosthetic socket in a bone cavity of a patient by placing a guide piece in bone that is close to the bone cavity, according to the position and alignment of a trial prosthetic socket (hereinafter a "trial") previously fitted in a desired position and alignment in the bone cavity and then, after removing the trial, positioning and aligning the prosthetic socket in the bone cavity using the guide piece's position and alignment for guidance. In some embodiments of the invention, a tilt (e.g. pitch and/or yaw) sensing device is used to show the tilt angle of devices used in the positioning and alignment procedure. For example, a tilt sensing device may be used in positioning and aligning the trial. In some embodiments of the invention, the bone close to the bone cavity forms the bone cavity. The prosthetic socket fits in the bone cavity and proper positioning and alignment of the prosthetic socket involves creating a peg positioning bore in the bone using the trial to define the position and alignment of the peg positioning bore. The drill creating the peg positioning bore may comprise a tilt sensing device to provide additional guidance for the position and alignment of the peg positioning bore. A peg of the prosthetic socket is then fitted into the peg positioning bore to help hold the prosthetic socket in the desired position and alignment. In addition to the peg positioning bore, a tilt sensing device on a prosthetic socket driver or on a guiding device used to place and/or secure the prosthetic socket in the bone cavity, guides proper positioning and alignment of the prosthetic socket into the bone cavity.

In one embodiment of the invention, proper positioning and alignment includes creating the peg positioning bore in the bone forming the bone cavity. The position of the peg positioning bore is guided by a drill guide channel in the trial. A drill guide is then placed in the peg positioning bore. The placing of the drill guide may be done with the aid of a tilt sensing device attached to the drill guide. This drill guide is a cannulated tube and sleeve and may be made of metal such as a cobalt/chrome alloy. "Cannulated" herein means to have an appropriately sized lumen. A guide piece such as a Kirschner wire is then placed through the cannulated portion of the drill guide and drilled or pushed into the bone. The lumen of the cannulated drill guide is sized to correspond to the guide piece (the lumen is just big enough to allow the guide piece to pass through the drill guide). Thus, the angle in which the guide piece is placed into the bone is defined by the drill guide. This angle will be the same angle the trial was in when properly positioned. The drill guide and trial are then removed leaving the guide piece in the bone.

To position the prosthetic socket in the exact location and angle as the trial (when the trial was fitted in the bone cavity) a peg (having a lumen sized to correspond to the guide piece) of the prosthetic socket is slid over the guide piece and the peg fitted into the peg positioning bore. Properly positioned by guidance of the guide piece and the peg in the peg positioning bore, the prosthetic socket is securely fastened to the bone by driving it in place using a prosthetic socket driver. The prosthetic socket driver may have a hollow portion so that it may be used while the guide piece is still in place. Additionally, in some embodiments, the prosthetic socket driver may comprise a tilt sensing device to ensure the prosthetic socket is being driven exactly in a direction to achieve the desired position. The force applied to the prosthetic socket causes fins on the prosthetic socket to enter the bone and secure the prosthetic socket to the bone.

In another embodiment of the invention, the trial is placed in the bone cavity using a guiding device that comprises a tilt sensing device. Then, a peg positioning bore is created in the bone forming the bone cavity using a drill guide channel in the trial as a guide. A tilt sensing device attached to the drill that is used to create the peg positioning bore may provide additional guidance for creating the peg positioning bore. As such, the drill guide channel in the trial and the drill's tilt sensing device is used to establish the angle of the peg positioning bore being drilled in the bone. A modular extension of the guiding device is then fitted in the peg positioning bore. The guiding device's tilt sensing device is again used to ensure the guiding device is positioned in a particular direction. The guiding device also has a tubular pin guide, such as a Steinman pin guide, fixedly attached to the guiding device. A guide piece is then drilled or pushed into bone close to the bone cavity using the tubular pin guide for guidance. The angle in which the guide piece is placed into the bone is established using the tubular pin guide (which is precisely parallel to the peg positioning bore) and the guiding device's tilt sensing device. The modular extension and trial are then removed from the bone cavity and the prosthetic socket is positioned in the bone cavity by positioning the prosthetic socket's peg in the peg positioning bore in one embodiment using the guiding device's driving plate in conjunction with the guide piece and the tilt sensing device. Once the prosthetic socket is positioned and aligned in the bone cavity, it has to be driven firmly in place. This is done by placing the driving plate (driver) on the face of the prosthetic socket and using the guide piece and the tilt sensing device to align the driving plate to drive the prosthetic socket with the peg into the peg positioning bore at the proper angle.

BRIEF DESCRIPTION OF THE DRAWINGS

For a more complete understanding of the present invention, reference is now made to the following descriptions taken in conjunction with the accompanying drawings, in which:

FIGS. 3A-3E show trials according to embodiments of the invention;

FIGS. 10A-10G show how a guiding device is used to position and align a prosthetic socket according to one embodiment of the invention;

DETAILED DESCRIPTION OF THE INVENTION

Figure 1A:
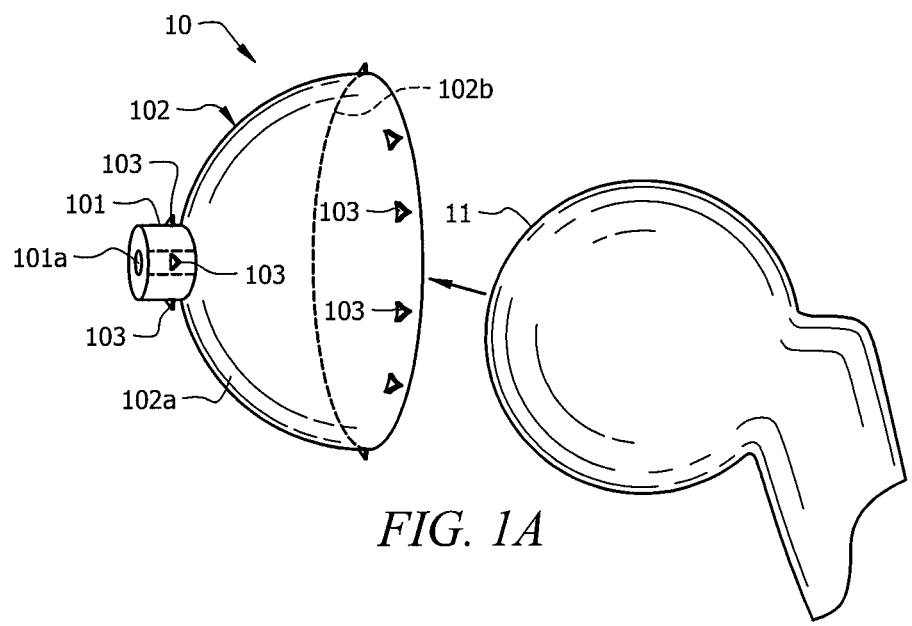
FIG. 1A shows a prosthetic socket and ball according to one embodiment of the invention.
Figure 1B:
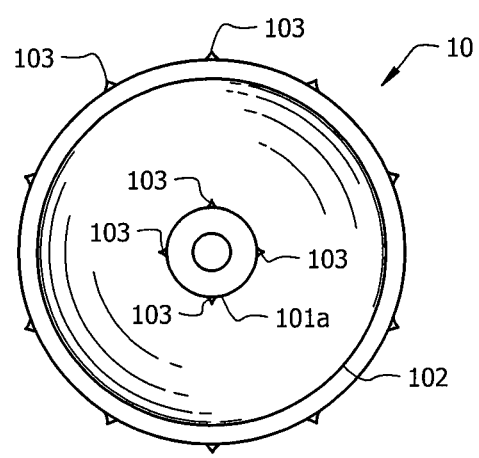
FIG. 1B shows a prosthetic socket according to one embodiment of the invention.

FIG. 1 shows a prosthetic socket 10 and a prosthetic ball 11 according to one embodiment of the invention. Prosthetic socket 10 may include a peg 101. Peg 101 may have a lumen 101a. Prosthetic socket 10 also has a hemispherical portion 102. Hemispherical portion 102 has an outer portion 102a that fits into the bone cavity of a patient. The inner portion 102b of hemispherical portion 102 receives prosthetic ball 11. Outer portion 102a may have fins 103 for securing prosthetic socket 10 to bone. Peg 101 may also include fins 103 to help secure peg 101 to bone. Prosthetic socket 10 may be made from material such as metal, composites, plastic or ceramic. The composites may comprise materials such titanium, titanium compounds, polymers, carbon nanotubes and the like. Prosthetic ball 11 may be made of metal or ceramic. Outer portion 102a is rough and thereby specially adapted to facilitate bone growth into prosthetic socket 10 to help hold prosthetic socket 10 in place. Typically, the metal used in the prosthetic devices is titanium because titanium is very compatible with bone.

Figure 8A:
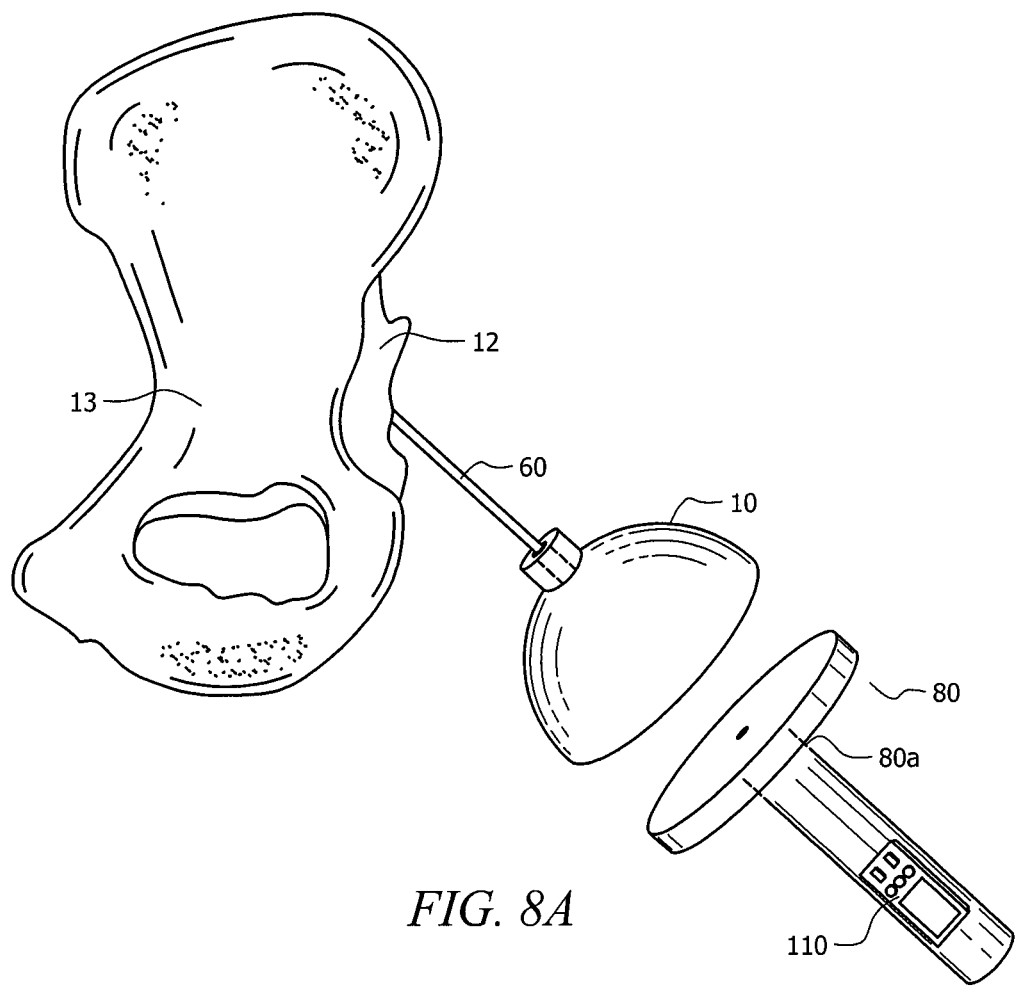
FIGS. 8A and 8B show how a prosthetic socket is fitted to the acetabular region using a driving plate and a cannulated shaft.
Figure 8B:
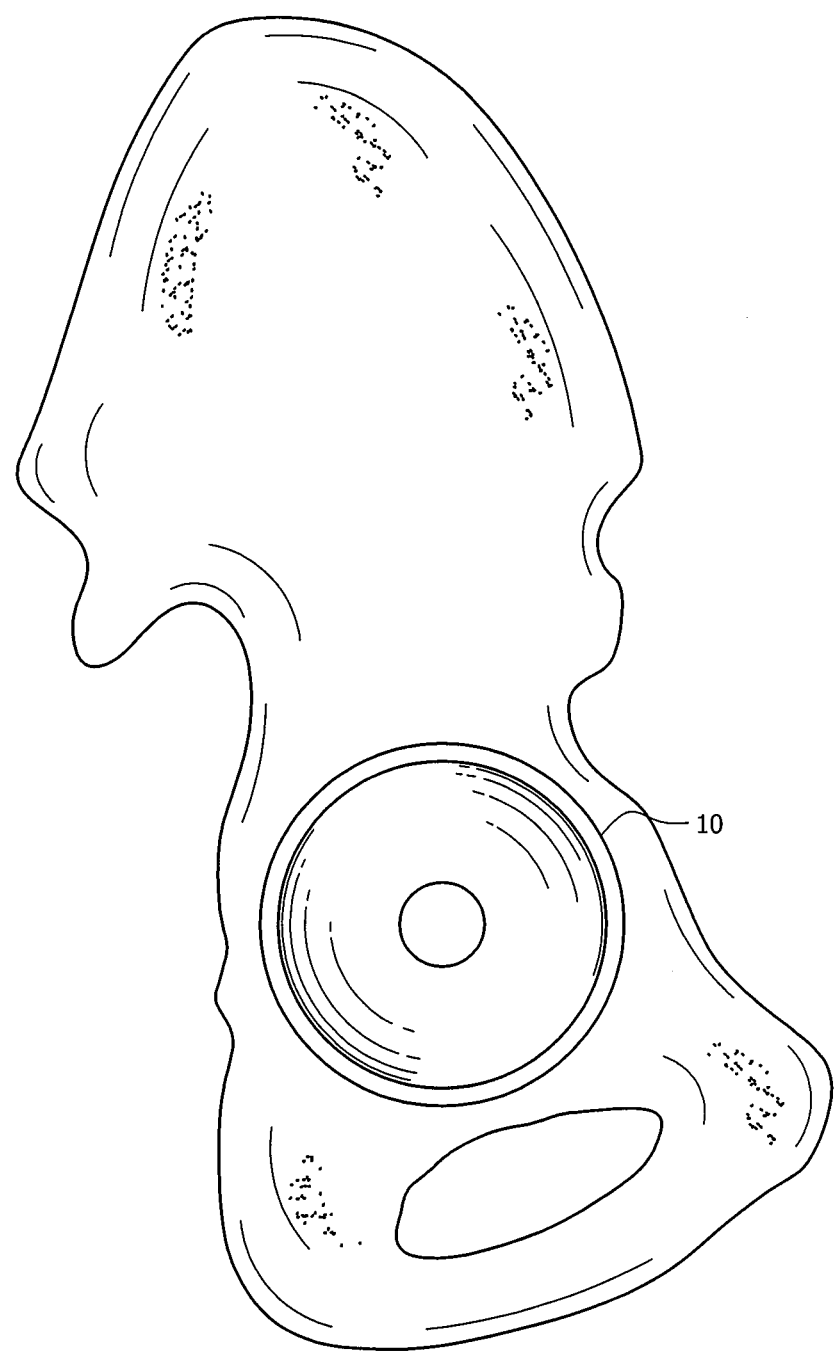

In some cases both the prosthetic ball and socket are metal. In other cases, the prosthetic socket is metal lined on the inner side with plastic or ceramic. Thus, the lining interfaces with prosthetic ball 11. The prosthetic ball may be metal or ceramic. Various combinations are possible and the concepts of the present invention are applicable to all these combinations (e.g., metal ball on metal socket, metal ball on plastic socket, ceramic ball on ceramic socket and ceramic ball on plastic socket). For hip replacement surgery, the prosthetic socket 10 is placed into the bone cavity 12 of the hip bone 13 (FIGS. 8A and 8B). Prosthetic ball 11 is then fitted into prosthetic socket 10. The hip replacement surgery also involves attaching prosthetic ball 11 to the femur or the thigh bone of the patient.

Figure 2:
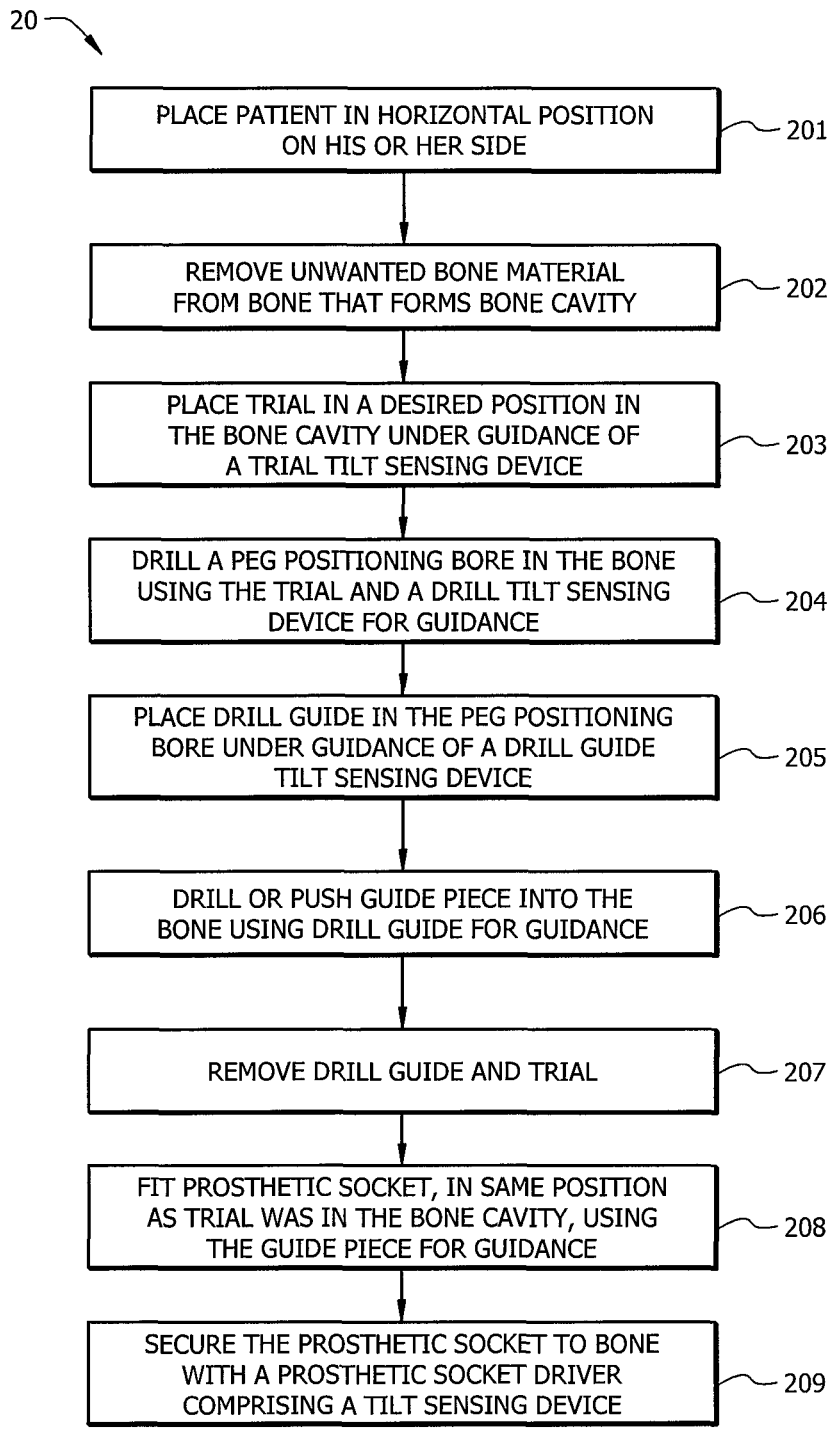
FIG. 2 shows a process to properly align a prosthetic socket according to one embodiment of the invention.
Figure 14A:
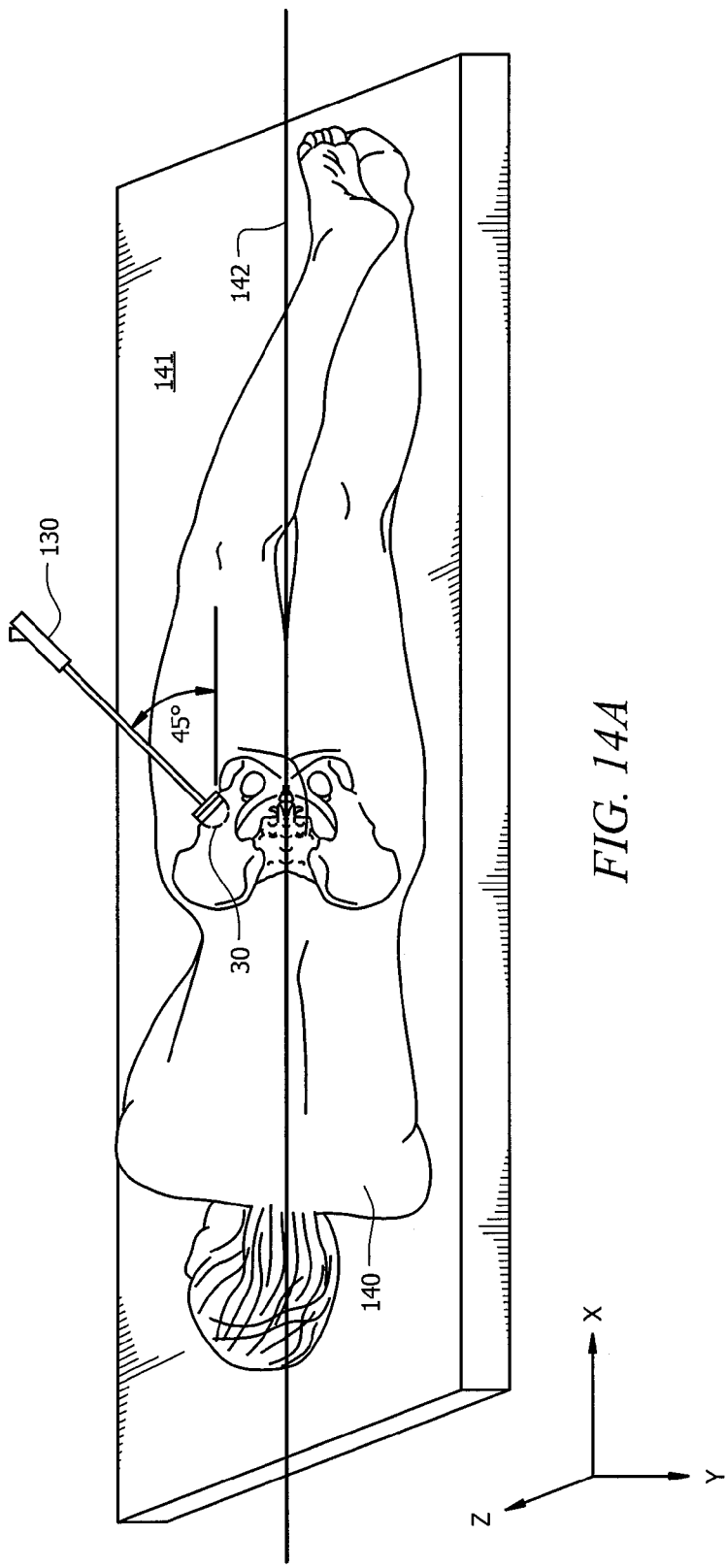
FIGS. 14A and 14B show the measurement of angles relative to imaginary planes through a patient's body.
Figure 14B:
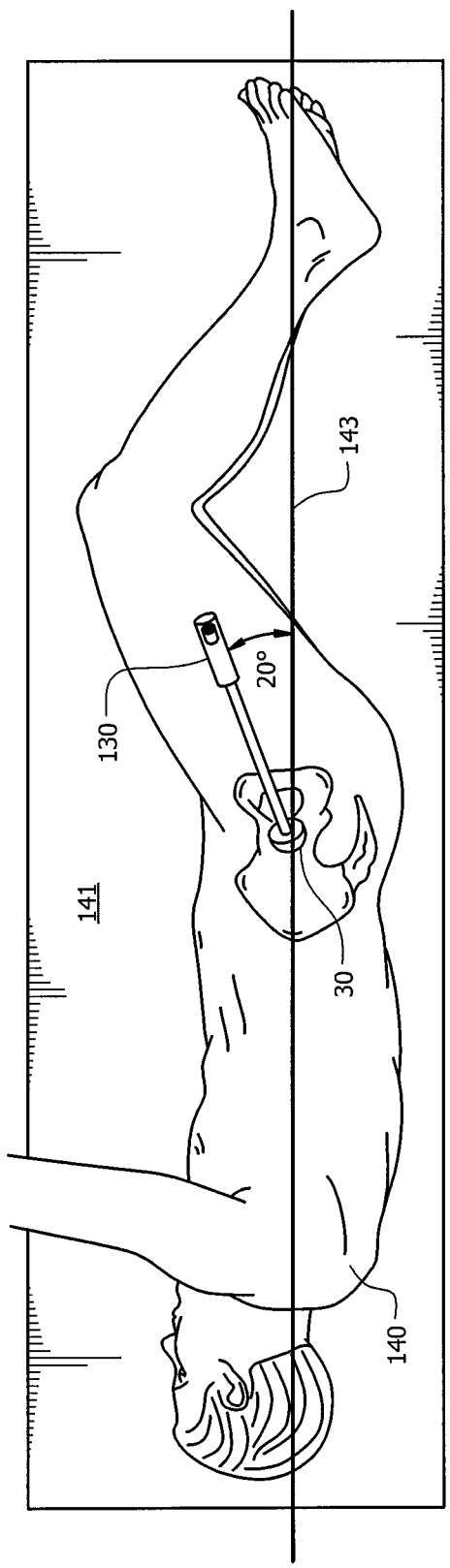

FIG. 2 shows process 20 of one embodiment of the invention which is a process to properly fit a prosthetic ball within the bone cavity of a patient. In process 201, the patient is positioned horizontally on his or her side as shown in FIGS. 14A and 14B. To ensure the patient is horizontal, the examination or operating table and floor should be flat. In process 202, the bone that forms bone cavity 12 is prepared by using power reamers to remove unwanted material such as arthritic bone. Further, enough material is removed so that bone cavity 12 is deep enough, sized and/or shaped to accept prosthetic socket 10.

In process 203, trial 30, as shown in FIG. 3, is then placed into bone cavity 12. Trial 30 has a drill guide channel 301 and a hemispherical shape conforming to the shape of bone cavity 12. Trial 30 is temporarily fitted in a desired position in bone cavity 12 and stabilized with short screws through screw holes 304, which are later removed. This desired position can be determined by various techniques such as manually by a practitioner based on experience, x-ray positioning, fluoroscopy or guidance by other electronic equipment. Additionally or alternatively, in one embodiment, the placing of trial 30 in bone cavity 12 is done under guidance of trial tilt sensing device 110 (shown in FIGS. 11A-11D).

Figure 11A:
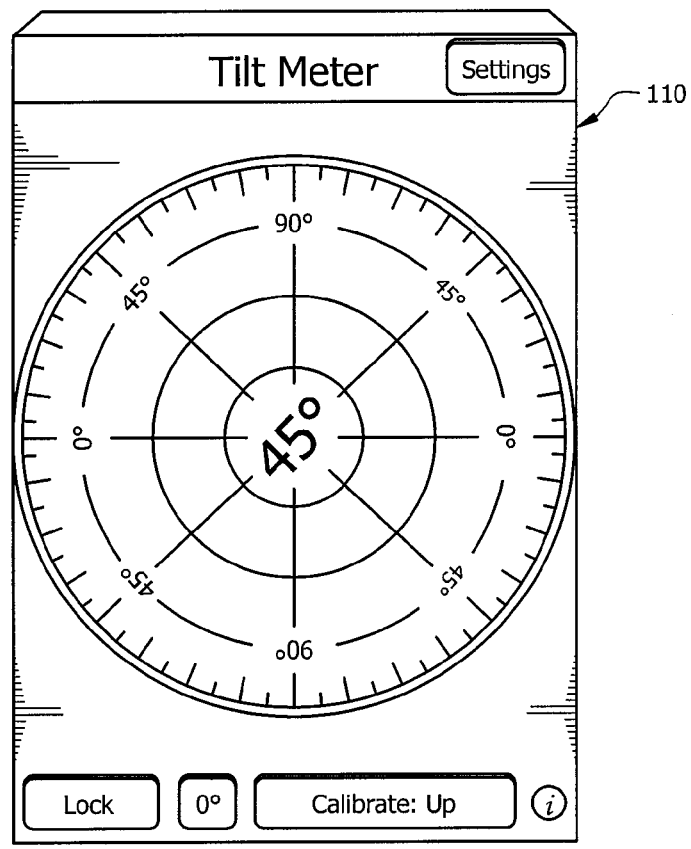
FIGS. 11A-11D show tilt sensing devices.
Figure 11B:
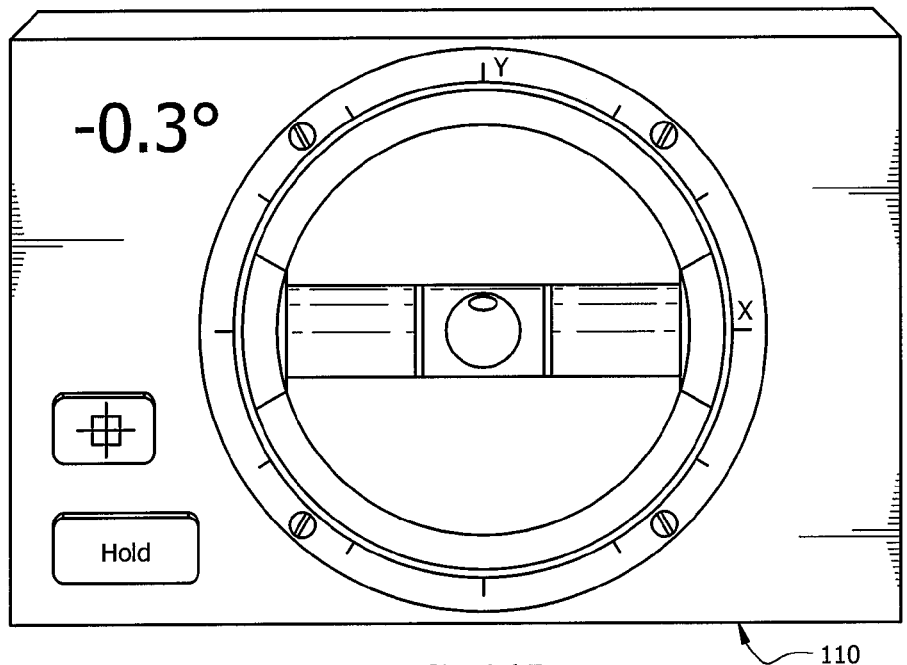
Figure 11C:
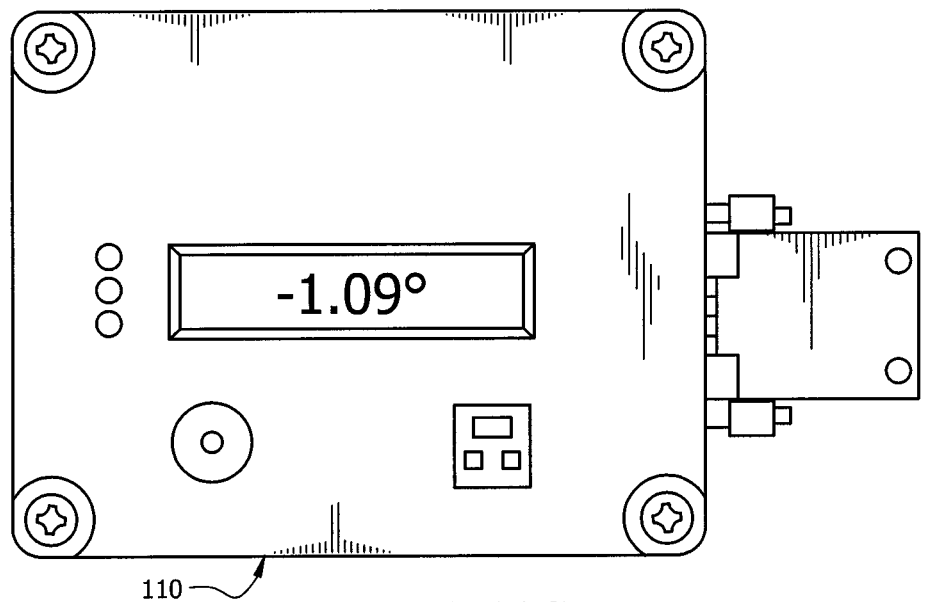
Figure 11D:
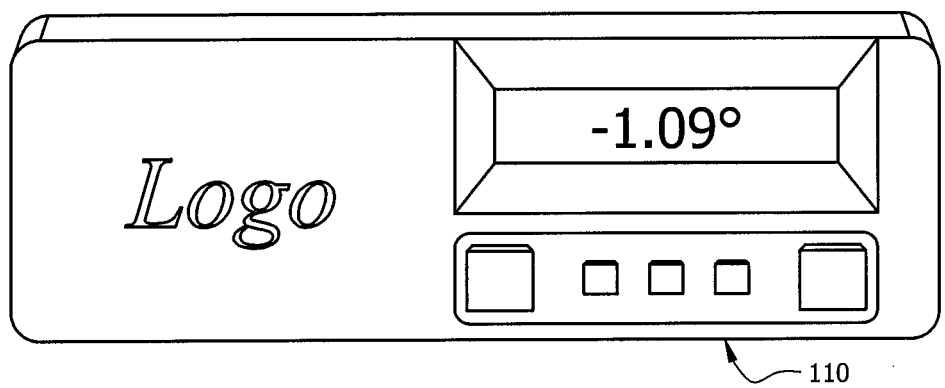

A tilt sensing device measures an angular tilt. The following are some of the types of tilt sensing devices: accelerometer, liquid capacitive, electrolytic, mercury, gas bubble liquid, pendulum and digital. Some tilt sensing devices measure the angle between a surface and a line or plane that is perpendicular to a line or plane through the earth's center of gravity. Other tilt sensing devices create an artificial horizontal plane and measure angular tilt based on this artificial horizontal plane. Tilt sensing device 110 may comprise a mechanical tilt sensing device as shown in FIGS. 11A and 11B or an electronic tilt sensing device as shown in FIGS. 11C-11D.

Figure 13:
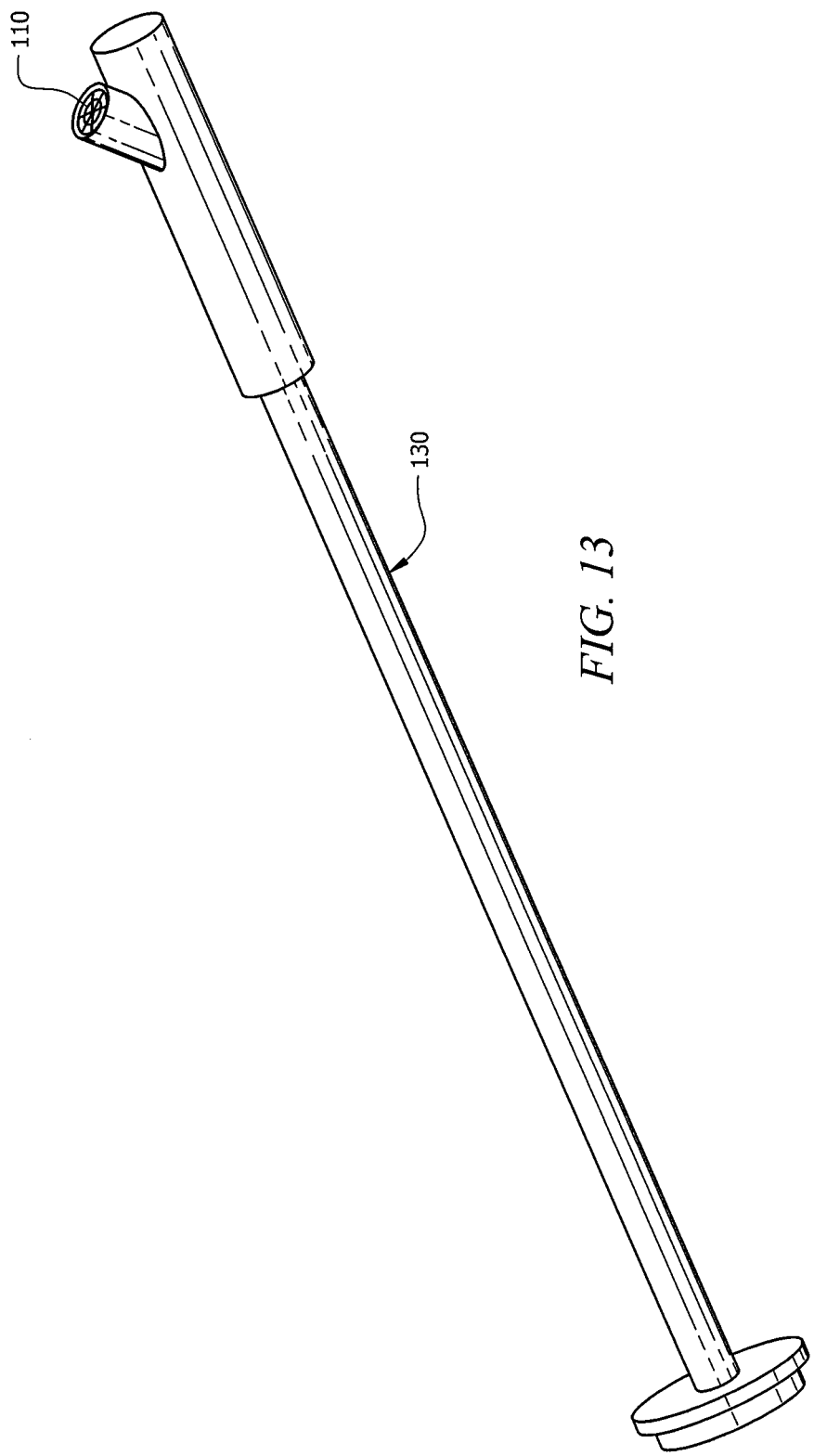
FIG. 13 shows a positioner/driver device according to one embodiment of the invention.

In carrying out the hip replacement procedures that require the guidance of tilt sensing device 110, the patient should be horizontal and positioned consistent with the planes used as the basis for the particular angle being measured. For example, FIG. 13 shows positioner/driver device 130 that is adapted to be used to position trial 30 or drive prosthetic socket 10 into the hip of patient 140. In FIG. 14A and FIG. 14B trial 30 is being positioned in the hip of patient 140. FIG. 14A shows the measurement of the abduction angle by tilt sensing device 110 which is attached to positioner/driver device 130. FIG. 14B shows the measurement of the anteversion angle by tilt sensing device 110. Patient 140 is on his or her side on operating table 141. Operating table 141 is horizontal. As such, sagittal plane 142 (an imaginary plane that divides the body into right and left sections) is parallel to operating table 141.

Therefore, the abduction angle of positioner/driver device 130 is the angle between positioner/driver device 130 and sagittal plane 142 as shown in FIG. 14A. The anteversion angle of tilt sensing device 110 is the angle between coronal plane 143 (an imaginary plane dividing the body into anterior and posterior portions) and positioner/driver device 130 As shown in FIG. 14B. It should be noted that coronal plane 143 and sagittal plane 142 are perpendicular to each other. In sum, to measure the abduction angle, the tilt sensing device should be calibrated/synchronized to measure 0° for sagittal plane 142. Similarly, to measure the anteversion angle, the tilt sensing device should be calibrated/synchronized to measure 0° for coronal plane 143.

Figure 4:
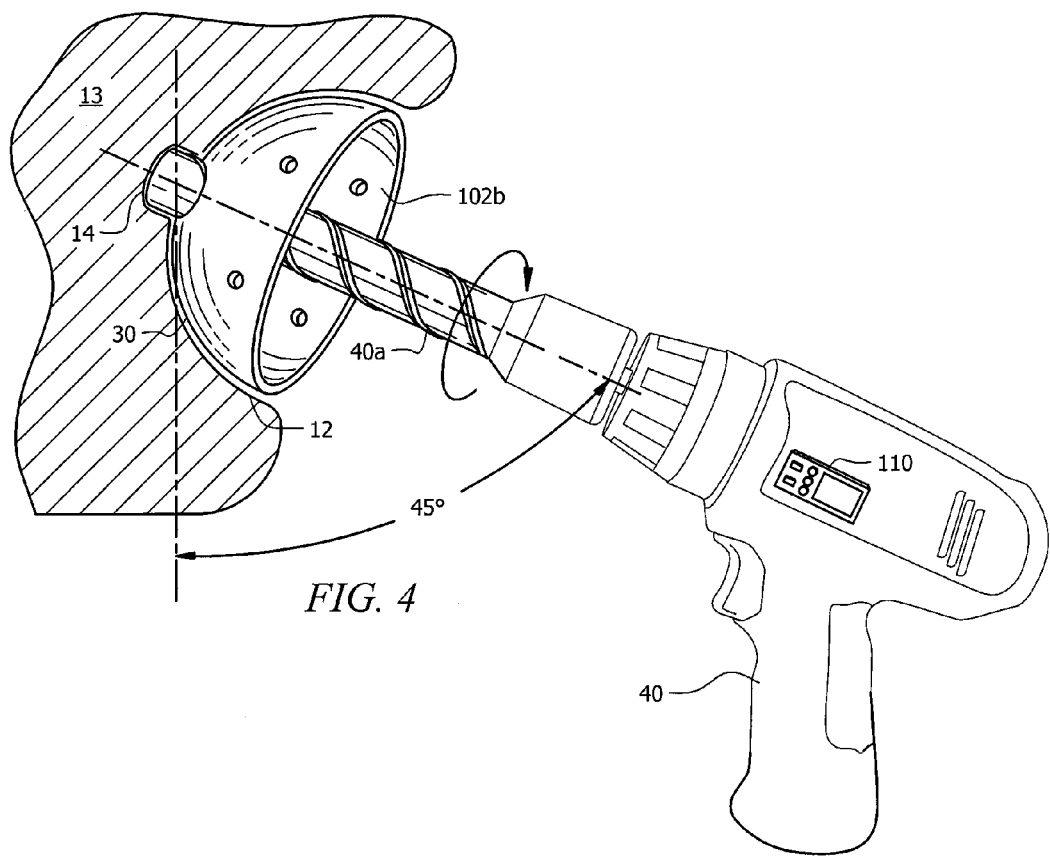
FIG. 4 shows a trial and drill in a bone cavity according to one embodiment of the invention.

Tilt Sensors are available from companies such as Microstrain®, and Rieker Incorporated. Further, a description of the operation of these types of devices may be found in U.S. Pat. No. 7,433,798 entitled "SOLID STATE ORIENTATION SENSOR WITH 360 DEGREE MEASUREMENT CAPABILITY," and U.S. Pat. No. 5,953,683 entitled "SOURCELESS ORIENTATION SENSOR," the complete disclosures of which are incorporated herein by reference. Some tilt sensing devices 110 are able to monitor angles in one plane. Other tilt sensing devices are able to monitor angles in a plurality of planes. For example, tilt sensing device 110 may be configured to monitor angles in the plane in which the abduction angle is measured, and also to monitor in the plane in which the anteversion angle is measured. In one embodiment, tilt sensing device 110 may be attached to extended drill guide channel 303 as shown in FIG. 3E. Drill guide channel 303 may be removed from dome 302 after trial 30 is properly positioned in bone cavity 12. In some embodiments of the invention, a liner may be placed in trial 30 and a trial reduction performed. Trial reduction involves placing and maneuvering a prosthetic ball in the liner (which is in the fitted trial) to check for proper alignment, stability and range of motion. Once trial 30 is in the desired position, in process 204, a peg positioning bore 14 is drilled in bone 13 that forms bone cavity 12 by placing drill bit 40a through drill guide channel 301, as shown in FIG. 4.

It should be noted that drill guide channel 301 has a channel that guides or channels drill bit 40a to precisely correspond with the alignment of trial 30. Additionally, drill 40 may be fitted with tilt sensing device 110 to ensure the proper angle corresponding to the alignment of trial 30 is maintained at all times during the drilling. Thus, drill guide channel 301 and tilt sensing device 110 define the angle in which peg positioning bore 14 is being drilled by drill bit 40a.

Drill guide channel 301 defines the angle of peg positioning bore 14 by being only slightly larger in diameter than drill bit 40a so that drill bit 40a can enter the bone in one direction only. In some embodiments, drill bit 40a could have a much smaller diameter than drill guide channel 301. In such an embodiment, an appropriately sized bushing (to make up for the small diameter of drill bit 40a) could be placed on drill bit 40a and this bushing in conjunction with drill guide channel 301 would provide the proper alignment of drill bit 40a.

Apart from the diameter of (1) drill guide channel 301, or (2) drill guide channel 301 in conjunction with a properly sized bushing, a sufficient thickness "t" of dome 302 may help to ensure drill bit 40a does not have any "room to play" and can enter bone 13 in one direction only, as long as it is in drill guide channel 301. Alternatively, removable extension 303, which forms drill guide channel 301, may also be used to guide drill bit 40a at a specific angle into bone 13. Removable extension 303 may be connected to dome 302 by, for example, a screw and tapped hole mechanism. Peg positioning bore 14 is drilled into the bone to about one centimeter past dome 302.

Figure 5:
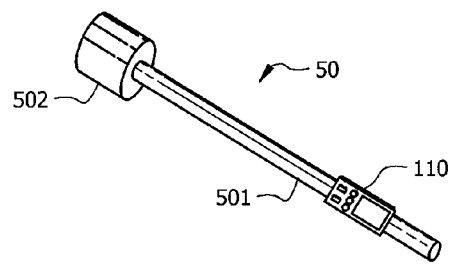
FIG. 5 shows a drill guide according to one embodiment of the invention.
Figure 6:
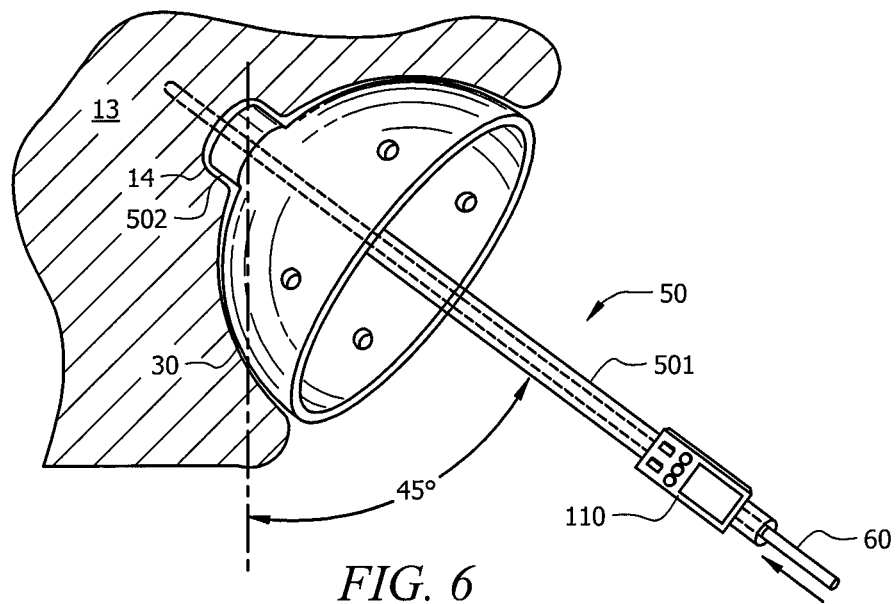
FIG. 6 shows the insertion of a guide into bone under guidance of a drill guide according to one embodiment of the invention.
Figure 7A:
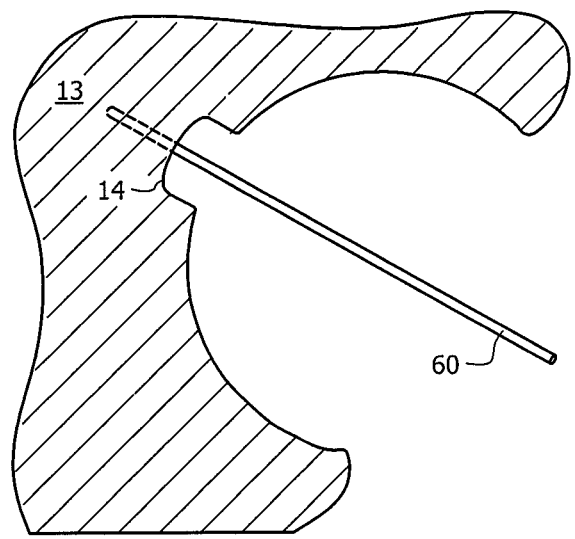
FIGS. 7A-7C show the use of a guide to properly align a prosthetic socket in a bone cavity.
Figure 7B:
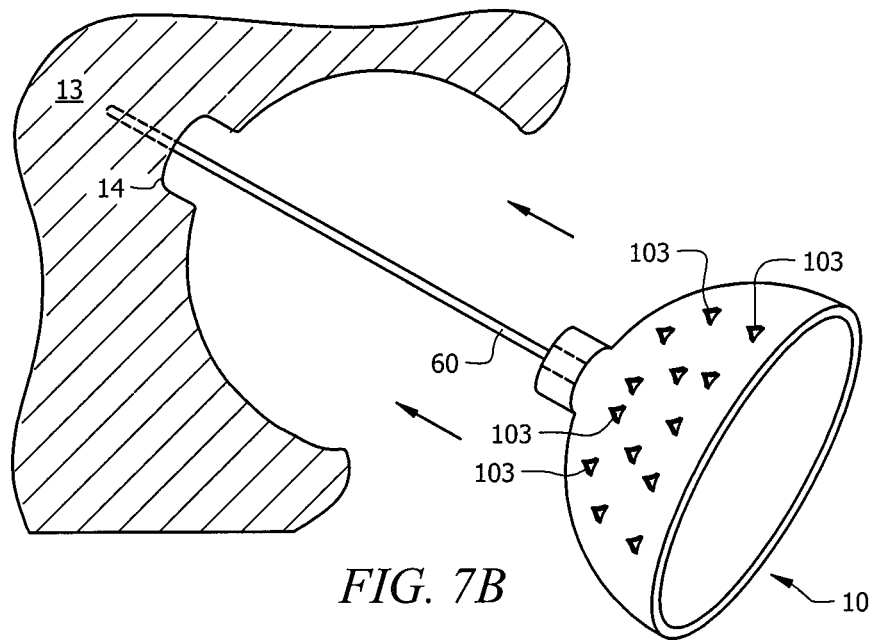
Figure 7C:
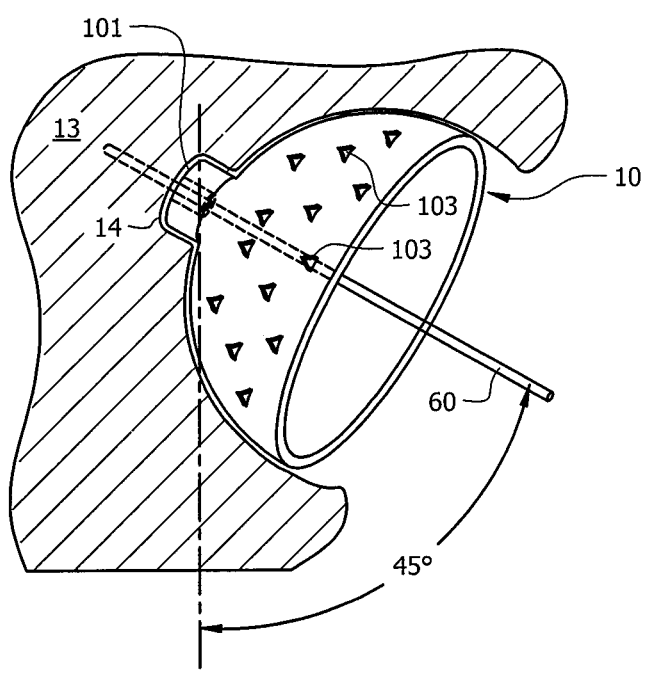

In process 205, drill guide 50, shown in FIG. 5, is placed into peg positioning bore 14. Drill guide 50 has a cannulated cylinder 501 and a cannulated sleeve 502. Cannulated cylinder 501 and cannulated sleeve 502 have lumens sized to accommodate guide piece 60. Sleeve 502 is slightly larger than drill bit 40a and therefore fits tightly into the peg positioning bore 14 at the same angle drill bit 40a entered bone 13 under guidance of trial 30. Additionally, the placing of drill guide 50 may be done under guidance of trial tilt sensing device 110 attached to drill guide 50. As shown in FIG. 6, drill guide 50 is then used as a guide to insert a guide piece 60 into bone 13, in process 206. In this process, because drill guide 50 is located in bone 13 in a position and alignment according to the position and alignment of trial 30 and the lumen of drill guide 50 precisely guides guide piece 60 into bone 13, then guide piece 60 is inserted in bone 13 according to the position and alignment of trial 30. Moreover, in embodiments that include tilt sensing device 110, tilt sensing device 110 may be used to ensure that drill guide 50's proper position and alignment is maintained throughout the procedure. In another embodiment of the invention, instead of placing drill guide 50 into peg positioning bore 14, it could be placed in drill guide channel 301 while providing guidance for the insertion of guide piece 60 into bone 13.

Guide piece 60 may be inserted about one centimeter into bone 13. In this process, guide piece 60 may be drilled or pushed into bone 13. Guide piece 60 may be a Kirschner wire or other appropriate wire, pin rod etc. Because drill guide 50 is used to guide guide piece 60 into bone 13, guide piece 60 enters bone 13 at the same position and direction as drill bit 40a did. As such, guide piece 60 is an indicator of the position of trial 30 when trial 30 was fitted in bone cavity 12. FIGS. 4-8 illustrate the acetabula. Therefore, the abduction angle of trial 30 is about 40° to 45° as shown and the anteversion angle is 10° to 20°.

In process 207, drill guide 50 and trial 30 are removed from bone cavity 12 leaving guide piece 60. In process 208, prosthetic socket 10 is positioned, in the same position and angle as the trial was, using guide piece 60 for guidance. To do so, prosthetic socket 10 is placed over the guide piece 60 so that guide piece 60 fits into lumen 101a of peg 101. Prosthetic socket 10 is then slid along guide piece 60 into bone cavity 12. Peg 101, which has a slightly larger diameter than drill bit 40a (and thus peg positioning bore 14), is positioned in peg positioning bore 14 prior to more secure fastening to bone 13.

Process 209 involves securing the prosthetic socket to bone 13, as illustrated in FIGS. 8A and 8B. This is done by using a prosthetic socket driver 80. Prosthetic socket driver 80 may have an aperture 80a in it that allows prosthetic socket driver 80 to fit over guide piece 60 as prosthetic socket driver 80 is used to tap prosthetic socket 10 in place. Additionally, prosthetic socket driver 80 may comprise a tilt sensing device 110. Thus, tilt sensing device 110 attached to prosthetic socket driver 80 may be used to guide the process of driving prosthetic socket 10 in at the correct angle. Prosthetic socket 10 is tapped in place to loosely engage bone 13 in the desired position. Guide piece 60 is then removed providing more room for prosthetic socket 10 to be more forcefully driven in place by prosthetic socket driver 80. Here, tilt sensing device 110 attached to prosthetic socket driver 80 continues to provide guidance for the driving process in the absence of guide piece 60. In another embodiment of the invention, in process 209, guide piece 60 may be kept in place in bone 13 to guide the forceful driving of prosthetic socket 10 in place by prosthetic socket driver 80. After prosthetic 10 is securely in place, in this latter embodiment, guide piece 60 is removed.

Figure 9:
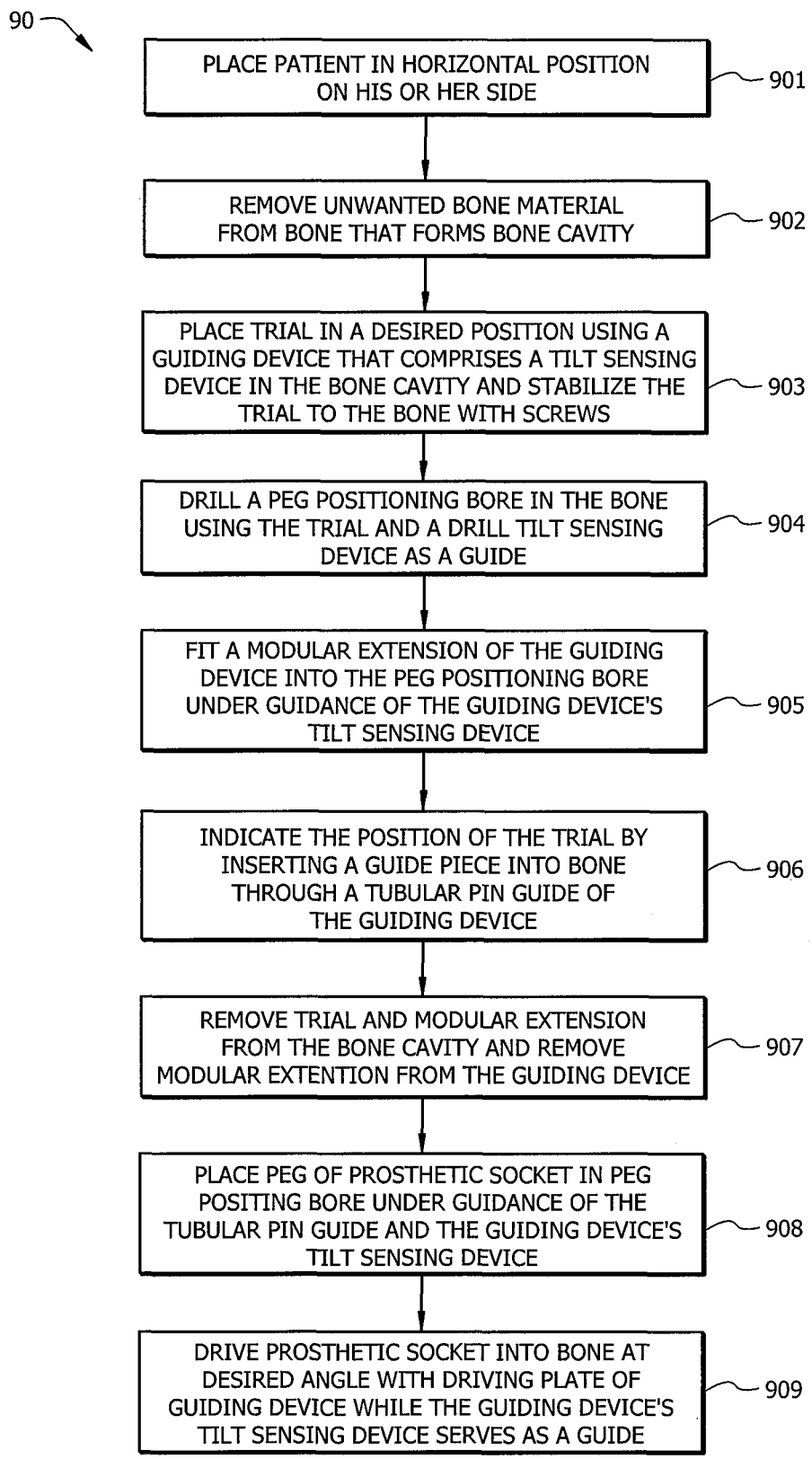
FIG. 9 shows a process to properly align a prosthetic ball according to one embodiment of the invention.
Figure 10A:
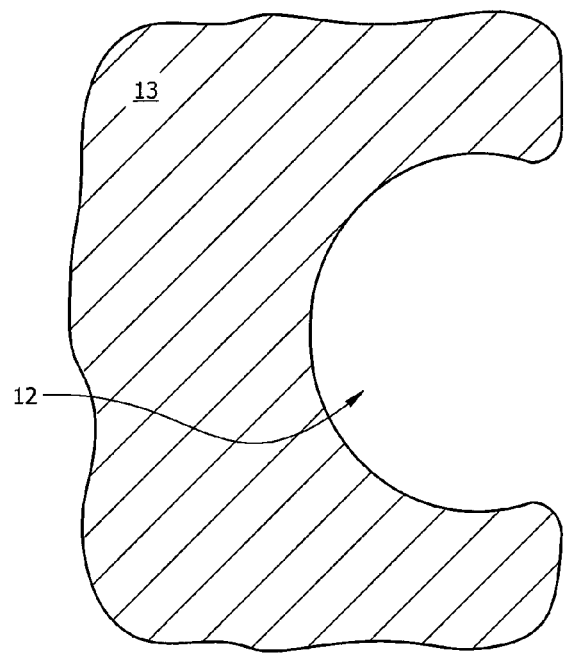
Figure 10B:
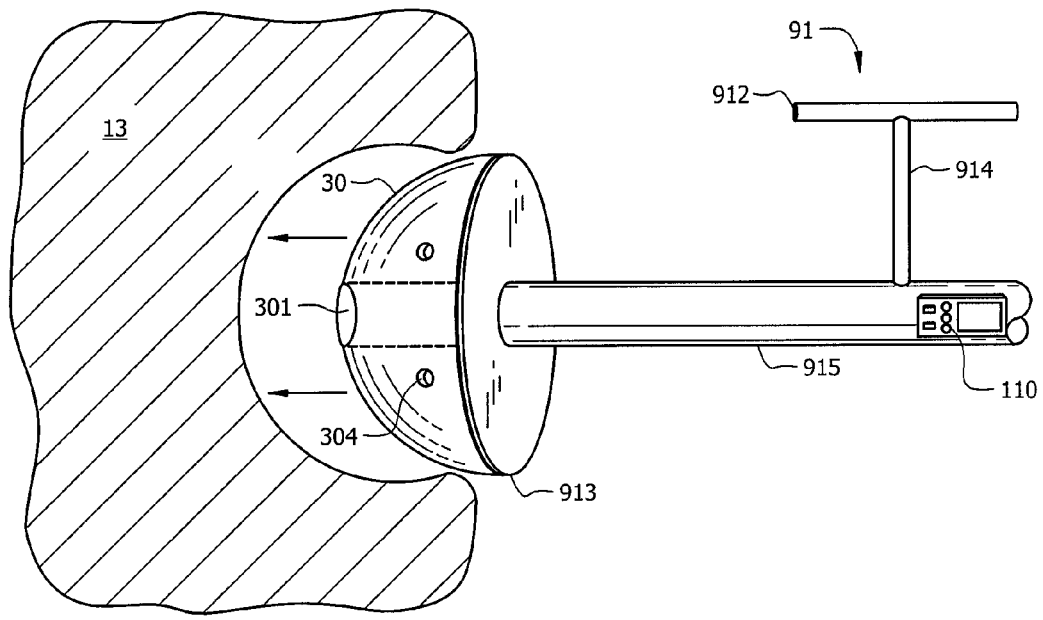
Figure 10C:
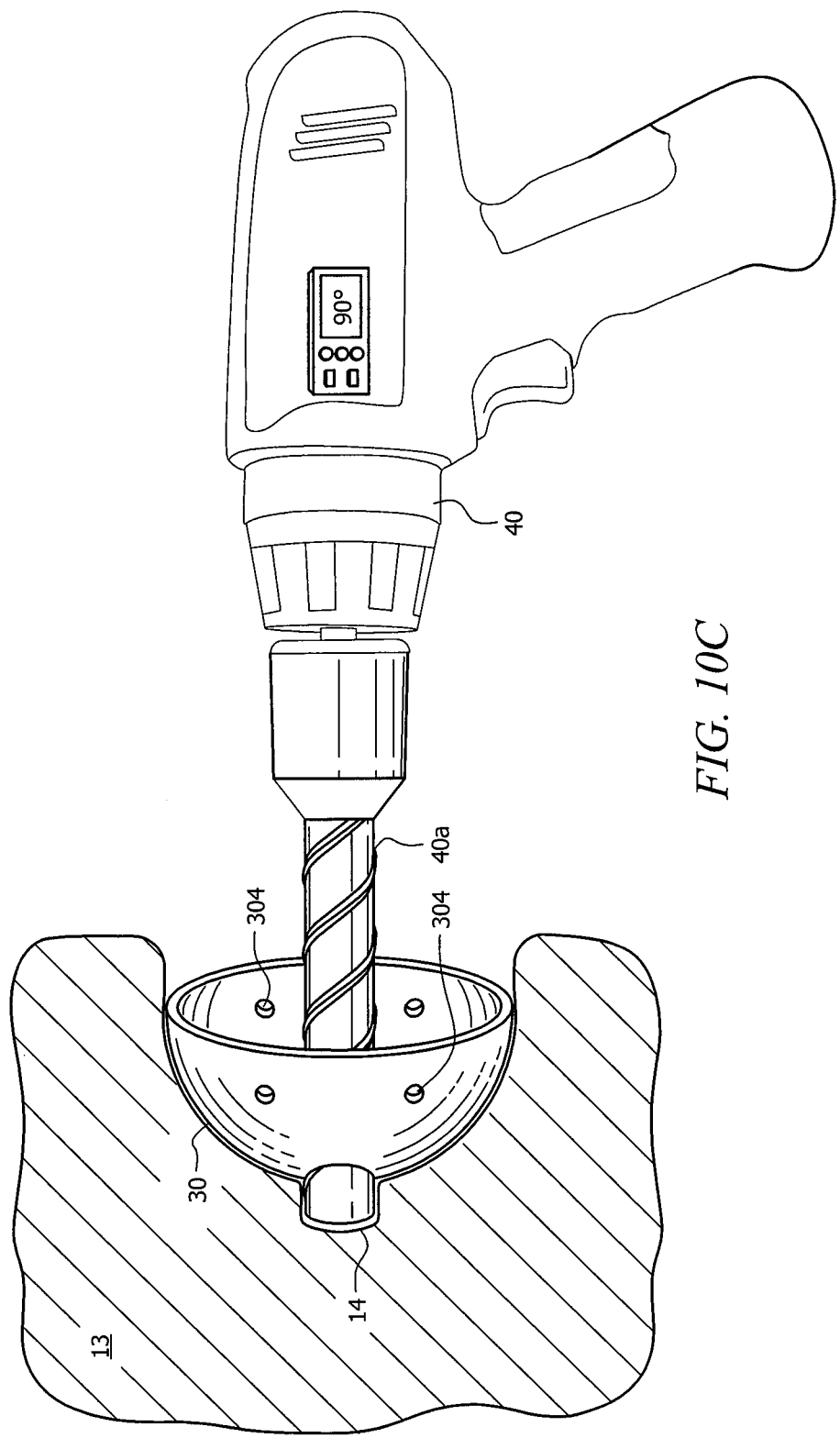

FIG. 9 shows process 90, another embodiment of the invention, that properly fits a prosthetic socket within the bone cavity of a patient. In process 901, the patient is positioned horizontally on his or her side as described in process 201 above. In process 902, the natural bone socket is prepared for receiving prosthetic socket 10. As described above, this includes removal of bone so that bone cavity 12 (illustrated in FIG. 10A) is deep enough to receive prosthetic socket 10 and also to remove arthritic material. Process 903 involves fitting trial 30 into a desired position in bone cavity 12. The fitting of trial 30 may involve the use of guiding device 91 which comprises tilt sensing device 110. To fit trial 30 using guide piece 91, modular extension 911 (sized to fit in guide channel 301) is inserted in guide channel 301. Then modular extension 911, with trial 30 positioned on it, is placed in bone cavity 12 while tilt sensing device indicates a desired abduction and/or anteversion angle as shown in FIG. 10B. Once placed in the desired position, trial 30 is stabilized by temporarily screwing it in place through screw holes 304. Once trial 30 is stabilized in the desired position, peg positioning bore 14 is drilled into bone 13 through drill guide channel 301 of trial 30, in process 904 and as shown in FIG. 10C. Drill guide channel 301, as discussed earlier, defines the angle in which drill bit 40a enters bone 13. In other words, trial 30 guides drill bit 40a into bone 13 at a particular angle. Additionally, drill bit 40a may comprise a tilt sensing device for ensuring that drill 40 drills peg positioning bore at the correct angle into bone 13.

Figure 10D:
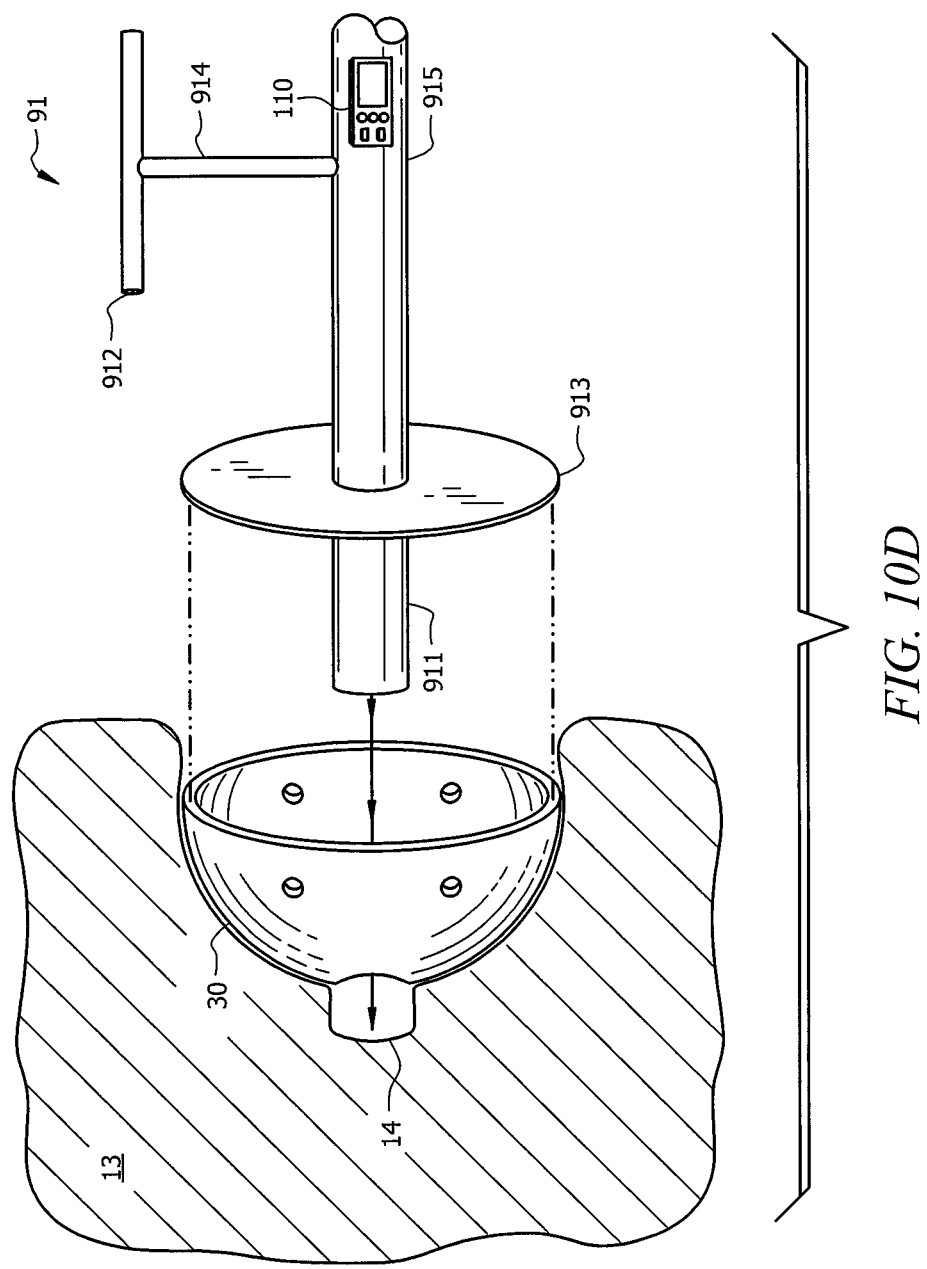
Figure 10E:
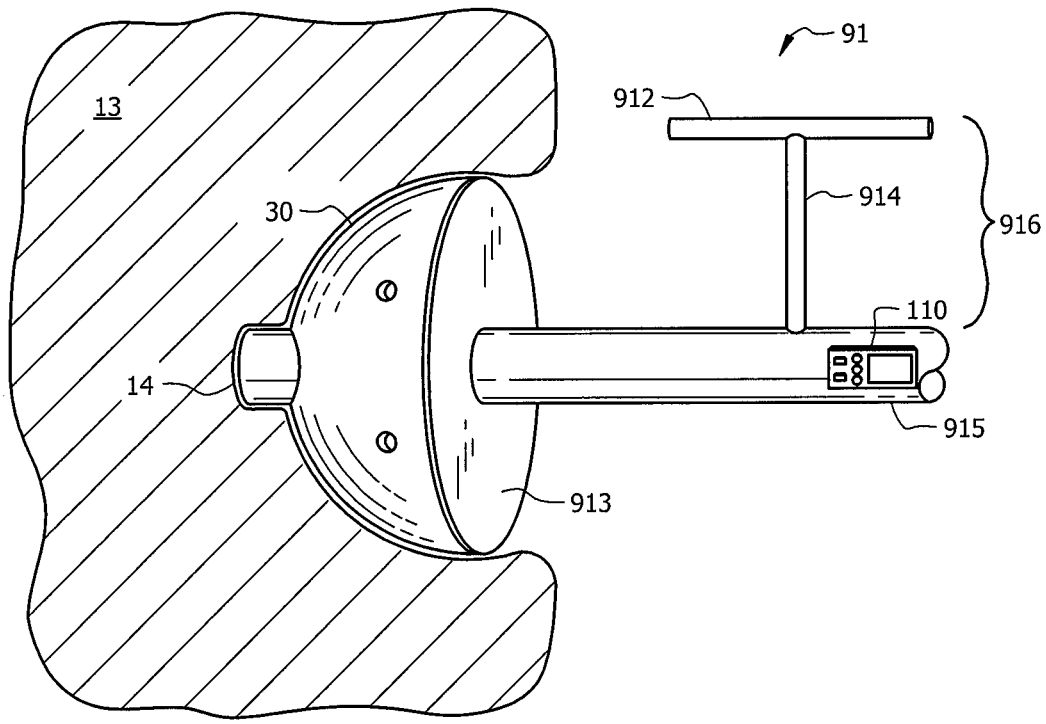

In process 905, drill bit 40a is removed and modular extension 911 of guiding device 91 is inserted into peg positioning bore 14 as illustrated in FIGS. 10D-10E. Tilt sensing device 110 of guiding device 91 is used to guide the insertion of modular extension 911 into peg positioning bore 14 at the desired angle. Guiding device 91 of one embodiment is used to properly fit prosthetic sockets into bone cavities and thus may include a driving plate 913. Tubular pin guide 912 is fixedly attached to portion 915 by connector 914. Tubular pin guide 912 and connector 914 form guide tower 916. Modular extension 911 is removably attached to portion 915. As such, for any direction in which modular extension 911 is pointed, tubular pin guide 912 will point in the corresponding direction.

Figure 10F:
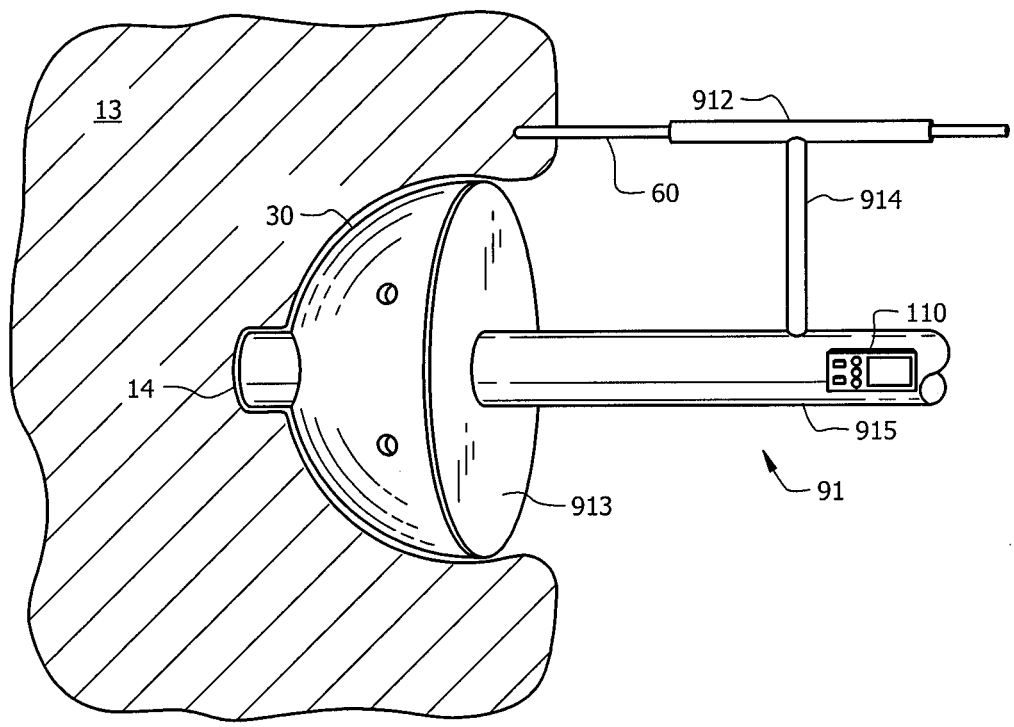

Modular extension 911 is positioned in peg positioning bore 14, at the same angle as drill bit 40a entered bone 13. This position and angle are indicated by tubular pin guide 912. To indicate the position and angle, in process 906, guide piece 60, such as a Steinman pin, is pushed through tubular pin guide 912 into bone close to bone cavity 12 as shown in FIG. 10F. At this point, driving plate 913 rests on the face of trial 30. The angle in which guide piece 60 is placed into bone 13 is defined by tubular pin guide 912 because the lumen of tubular pin guide 912 is precisely sized to guide guide piece 60 in a particular direction when guide piece 60 is placed in the lumen of tubular pin guide 912. In turn, the position of tubular pin guide 912 is determined by the angle modular extension 911 is set into peg positioning bore 14. Additionally, guiding device 91's tilt sensing device 110 is used to ensure the proper positioning and alignment of guiding device 91.

In process 907, trial 30 is removed from bone cavity 12. Guiding device 91 is also removed from bone cavity 12 and modular extension 911 removed from guiding device 91. At this point, guide piece 60 is still positioned in bone 13. Using guide piece 60 in conjunction with guiding device 91 as shown in FIG. 10G, prosthetic socket 10 is positioned in the exact position and alignment as trial 30 was when trial 30 was properly positioned in bone cavity 12. To do so, in process 908, peg 101 of prosthetic socket 10 is placed in peg positioning bore 14. Driving plate 913 may be used to align prosthetic socket 10 as peg 101a is being fitted in peg positioning bore 14.

At this point, prosthetic socket 10 is loosely engaged to bone 13. In process 909, a force is applied to driving plate 913 to drive prosthetic socket 10 firmly into peg positioning bore 14 at the same angle trial 30 was when it was fitted in bone cavity 12, as shown in FIG. 10G. In process 909, directional guidance is provided by guide piece 60 and/or tilt sensing device 110. It should be noted that peg 101 does not need to be cannulated and, thus, in some embodiments there is no lumen in peg 101.

In embodiments of the invention, various prosthetic alignment devices such as trial 30, drill 40, drill guide 50, prosthetic socket driver 80 and guiding device 91 are disclosed as comprising a tilt sensing device 110. Because trial 30, drill 40, drill guide 50, prosthetic socket driver 80 and guiding device 91 must be sterile when initially used on a patient, these devices may be either disposable or capable of undergoing sterilization by heat, chemicals and the like. In the cases where the devices are capable of being sterilized, tilt sensing device 110 should be detachable from trial 30, drill 40, drill guide 50, prosthetic socket driver 80 and guiding device 91 because the sterilization process would destroy the tilt sensing device depending on the configuration and sterilization method used. In a case where tilt sensing device would be destroyed by sterilization, the tilt sensing device 110 would be discarded after use.

In other embodiments, tilt sensing device 110 may be configured to undergo certain types of sterilization and thus may be detached from the alignment devices to allow such sterilization and then reused with the alignment device which may have been sterilized by a different process. Tilt sensing device 110 may be made detachable from the alignment device by, for example, providing a cavity in the alignment device properly sized so that tilt sensing device 110 may be snapped into the cavity prior to surgery and later pried out of the cavity after surgery.

Figure 12:
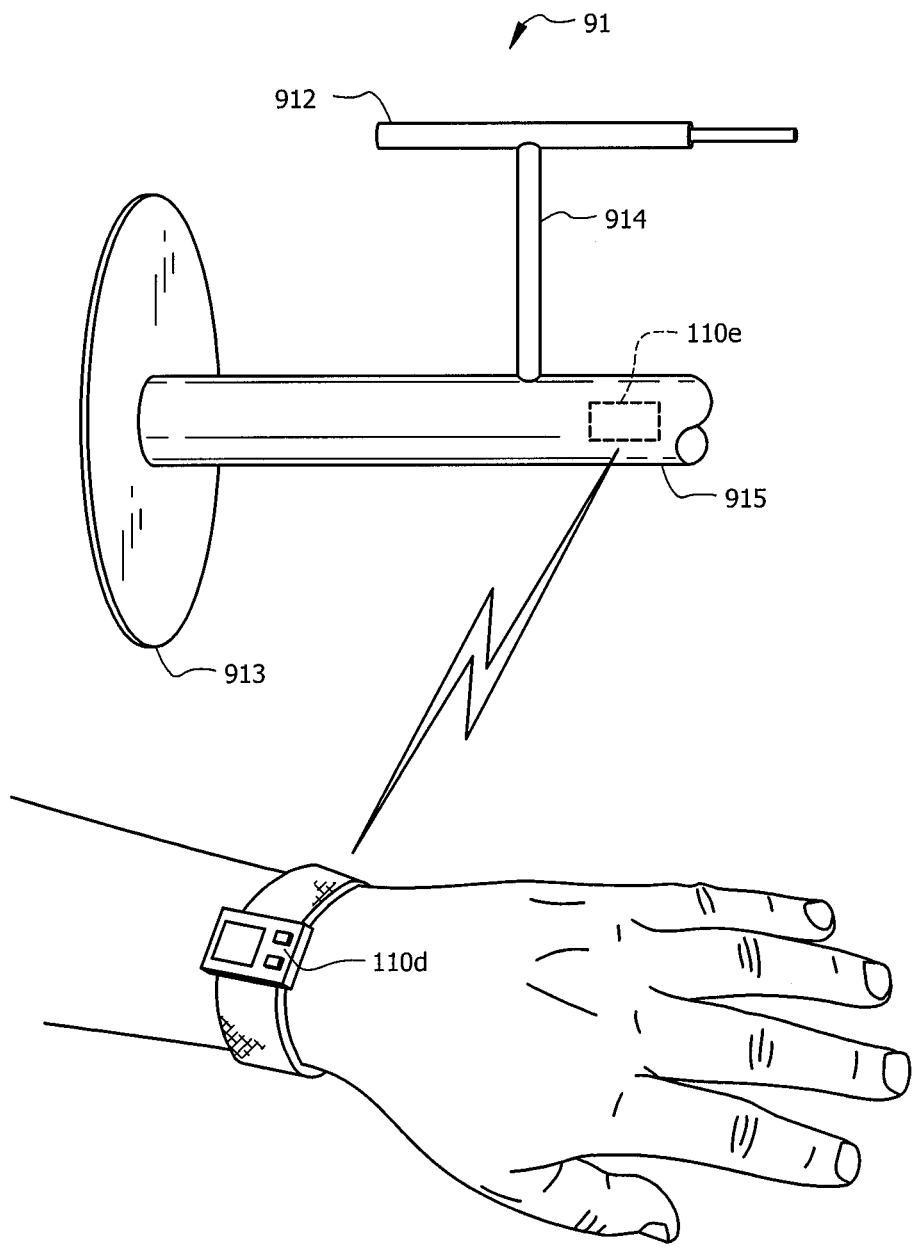
FIG. 12 shows a prosthetic positioning and aligning system according to one embodiment of the invention.

In one embodiment of the invention, to avoid the discarding of the tilt sensing device, the tilt sensing device is divided in two parts—tilt sensing device electronics 110E comprising a transmitter and tilt sensing display 110D comprising a receiver as shown in FIG. 12. Tilt sensing device electronics 110E is capable of transmitting data to tilt sensing display 110D to cause tilt sensing display 110D to display the angle measured by tilt sensing device electronics 110E, though tilt sensing display 110D and tilt sensing device electronics 110E are apart from each other. Tilt sensing device electronics 110E is completely enclosed in the alignment device such as guiding device 91. Thus tilt sensing device electronics 110E is protected from heat and chemicals etc. during the sterilization of guiding device 91. Display 110D is remote from guiding device 91 and would not need sterilization as it is not placed in a patient's body. Instead, display 110D is placed in a location visible to the medical practitioner carrying out the hip replacement procedure but remote from sensing device electronics 110E.

In one embodiment, display 110D is configured to be worn on a medical practitioner's wrist. In another embodiment, display 110D is located on other operating room equipment that has patient monitors or in any other location in the operating room convenient to the medical practitioner. In some embodiments, though tilt sensing device 110 has both sensing device electronics and display in one unit, tilt sensing device 110 may be capable of transmitting data to a second display remote from tilt sensing device 110. Such second display may be located on other operating room equipment that has patient monitors.

It should be noted that the methods, devices and systems described herein are applicable to surgeries at different locations of the body. For example, the procedures described herein may be used in surgeries such as hip replacement surgery, shoulder replacement surgery and knee replacement surgery. Further, the methods, devices and systems include surgeries on humans and surgeries performed in the field of veterinary medicine.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A system for properly positioning and aligning a prosthetic socket in a patient, said system comprising:
   a trial having a central drill guide channel;
   a drill operable to drill a peg positioning bore in bone proximate to said bone cavity,
   wherein said drill guide channel is adapted to define an angle of said peg positioning bore being drilled in said bone;
   a drill guide having a cannulated tube and a cannulated sleeve, wherein said drill guide is further adapted for insertion and tight fit into said peg positioning bore and said drill guide channel;
   a guide piece adapted for insertion into said drill guide, wherein the angle in which said guide piece is placed into said bone is defined by the position of said drill guide in said peg positioning bore;
   a prosthetic socket with a peg, wherein a cannulated portion of said per is adapted to fit over said guide piece and said guide piece is adapted to guide said prosthetic socket, when said peg is slid over said guide piece, into a desired position in said bone cavity; and
   a tilt sensing device, said tilt sensing device attached to an alignment device, said alignment device selected from a list consisting of: said trial, said drill or said drill guide and configured to establish a particular angular tilt between said alignment device and a predetermined plane.

2. The system of claim 1 wherein said system is sterilazable.

3. The system of claim 1 wherein said tilt sensing device is removably attached to said alignment device.

4. The system of claim 1 wherein said plane is horizontal and said patient is lying horizontally.

5. The system of claim 1 wherein said particular angular tilt is an abduction angle.

6. The system of claim 5 wherein said abduction angle is 40° to 45°.

7. The system of claim 1 wherein said particular angular tilt is an anteversion angle.

8. The system of claim 7 wherein said anteversion angle is 10° to 20°.

9. The system of claim 1 wherein said tilt sensing device is configured to establish an abduction angle and an anteversion angle.

10. The system of claim 1 wherein said tilt sensing device is an electronic tilt sensing device.

11. The system of claim 1 wherein said predetermined plane is selected from the group consisting of: a sagittal plane and a coronal plane.

12. A system for properly positioning and aligning a prosthetic socket in a patient, said system comprising:
   a trial having a central drill guide channel;
   a drill operable to drill a peg positioning bore in bone proximate to said bone cavity, wherein said drill guide channel is adapted to define an angle of said peg positioning bore being drilled in said bone;

a drill guide having a cannulated tube and a cannulated sleeve, wherein said drill guide is further adapted for insertion and tight fit into said peg positioning bore and said drill guide channel;

a guide piece adapted for insertion into said drill guide, wherein the angle in which said guide piece is placed into said bone is defined by the position of said drill guide in said peg positioning bore;

a prosthetic socket with a peg wherein a cannulated portion of said peg is adapted to fit over said guide piece and said guide piece is adapted to guide said prosthetic socket, when said peg is slid over said guide piece, into a desired position in said bone cavity;

and wherein an alignment device, said alignment device selected from a list consisting of: said trial, said drill or said drill guide comprises a tilt sensing electronics encased in said alignment device, said electronics including a transmitter; and a tilt display remote from said alignment device, said tilt sensing device configured to establish a particular angular tilt between said alignment device and at least a plane selected from group consisting of: a sagittal plane and a coronal plane, said display comprising a receiver capable of receiving signals from said transmitter.

13. The system of claim 12 further comprising: a prosthetic socket driver, said prosthetic socket driver having a hollow portion operable to receive said guide piece.

14. The system of claim 12 wherein said tilt sensing device is capable of being sterilized without damage to said electronics.

15. The system of claim 12 wherein said display is configured to be worn on the wrist of a user.

* * * * *